United States Patent [19]

Sulkowski

[11] 3,994,920

[45] Nov. 30, 1976

[54] 5H-IMIDAZO[2,1-a]ISOINDOL-5-ONE COMPOUNDS

[75] Inventor: Theodore S. Sulkowski, Narberth, Pa.

[73] Assignee: American Home Products Corporation, New York, N.Y.

[22] Filed: June 2, 1966

[21] Appl. No.: 554,672

Related U.S. Application Data

[63] Continuation-in-part of Ser. Nos. 272,216, April 11, 1963, abandoned, and Ser. No. 444,050, March 30, 1965, abandoned.

[52] U.S. Cl. .................... 260/309.7; 260/239 BD; 260/329 F; 260/332.3 P; 260/332.5; 260/347.7; 424/244; 424/275; 424/278
[51] Int. Cl.² ................................... C07D 487/04
[58] Field of Search .......... 260/239 BD, 329, 332.3, 260/332.5, 347.7, 309.7

[56] References Cited
UNITED STATES PATENTS 3,334,113  8/1967  Houlihan ........................ 260/309.7

FOREIGN PATENTS OR APPLICATIONS 646,221  4/1964  Belgium ........................... 260/239

*Primary Examiner*—Natalie Trousof
*Attorney, Agent, or Firm*—Robert Wiser; John W. Routh

[57] ABSTRACT

A new class of chemical compounds whose members exert an appetite suppressant and mood elevating effect in man has been invented. This class is defined as being composed of those compounds having the 1-substituted-2,5-benzodiazocine structure, fully saturated in the nonbenzenoid portion, and whose nitrogens are tervalent. Members of this class are prepared by condensing an orthobenzoylbenzoic acid or ester thereof with an ethylenediamine and reducing with a metallic alkaline hydride the product thus obtained.

4 Claims, No Drawings

5H-IMIDAZO[2,1-a]ISOINDOL-5-ONE COMPOUNDS

This application is a continuation-in-part of applications Ser. No. 272,216 filed Apr. 11, 1963 and Ser. No. 444,050 filed Mar. 30, 1965, both of which are now abandoned.

This application relates to compositions of matter classified in the art of chemistry as substituted 2,5-benzodiazocines to intermediates for their preparation and to processes for making them.

The invention sought to be patented in its principal composition aspect is described as residing in the concept of a chemical compound having the 1-substituted-2,5-benzodiazocine structure, fully saturated in the non-benzenoid portion and whose nitrogens are tervalent.

The tangible embodiments of the principal composition aspect of the invention possess the inherent general physical properties of being crystalline solids, are substantially insoluble in water and are soluble in mineral acids, such as hydrochloric acid, in which they form dihydrochlorides. Examination of the compounds produced according to the methods hereinafter described reveals, upon infrared and nuclear magnetic resonance spectrographic analysis, spectral data supporting the molecular structures herein set forth. The aforementioned physical characteristics taken together with the elemental analysis, the nature of the starting materials and the mode of synthesis, confirm the structure of the composition sought to be patented.

The tangible embodiments of the invention possess the inherent applied use characteristics of exerting an appetite suppressant and mood-elevating effect in man, as evidenced by pharmacological and clinical evaluation according to standard test procedures.

As used herein, the term "benzodiazocine" is intended to include only those compounds wherein the heterocyclic ring carbon atoms are attached to exocyclic hydrogen or carbon atoms. It excludes those compounds wherein the carbon atoms may, for example, be doubly bonded to oxygen, the latter being more accurately termed "benzodiazocinones."

As used herein, the term "fully saturated in the non-benzenoid portion" refers to the atoms of the heterocyclic ring excluding the carbon atoms which are shared with the benzenoid portion of the nucleus. The bridging carbons as part of the aromatic ring system participate in the aromatic ring unsaturation.

As used herein, the term "tervalent" used in describing the nitrogen atoms of the heterocyclic portion of the nucleus means that the nitrogen atoms are not quaternary and do not bear a fourth alkyl group. The use of this term, however, is not intended to exclude the normal acid salts formed by neutralization of the basic amine function with pharmaceutically acceptable acids.

The invention sought to be patented in a second composition aspect is described as residing in the concept of a composition of matter formed by condensing an ortho-benzoylbenzoic acid, or an ester thereof, with an ethylenediamine.

The condensation is conducted in a non-reactive solvent or in an excess of one of the reactants, or preferably in pyridine, with heating until elimination of water or alcohol is complete, and separating the product produced therefrom.

The tangible embodiments of the second composition aspect of the invention possess the inherent general physical properties of being crystalline solids, are substantially insoluble in water and are soluble in mineral acids such as hydrochloric acid in which they form a hydrochloride. While the tangible embodiments of the second composition were formerly believed to be 3,4-dihydro-6-phenyl-2,5-benzodiazocin-1(2H)-ones, and were so described in the aforesaid prior applications, from the nature of the starting materials, the mode of synthesis, the product obtained on metal hydride reduction, their elemental analysis, and infrared and nuclear magnetic resonance spectrographic analysis, I have now confirmed that the tangible embodiments of the second composition aspect of the invention are in fact 9b-phenyl-1,2,3,9b-tetrahydro-5H-imidazo-[2,1-a]isoindol-5-ones.

The tangible embodiments of the second composition aspect of the invention possess the inherent applied use characteristics of being intermediates for the preparation of compositions possessing the inherent applied use characteristic of exerting an appetite suppressant and mood-elevating effect in man, as evidenced by pharmacological and clinical evaluation according to standard test procedures.

The invention sought to be patented in a principal process of making the composition aspect is described as residing in the concept of a sequence of reactions, including:

a. condensing an ortho-benzoylbenzoic acid or esteer thereof with an ethylenediamine, and, b. reducing the product obtained therefrom with a metallic hydride to obtain a 1-substituted-2,5-benzodiazocine fully saturated in the non-benzenoid portions and whose nitrogens are tervalent.

The manner of making and using the composition aspects of the invention and the process of the invention will now be generally described so as to enable a person skilled in the art of chemistry to make and use the same, as follows:

In describing the invention, reference will be made to the schematic illustration of the reaction sequence for preparing a specific embodiment of the invention below, wherein compounds are assigned Roman numerals sequentially for identification:

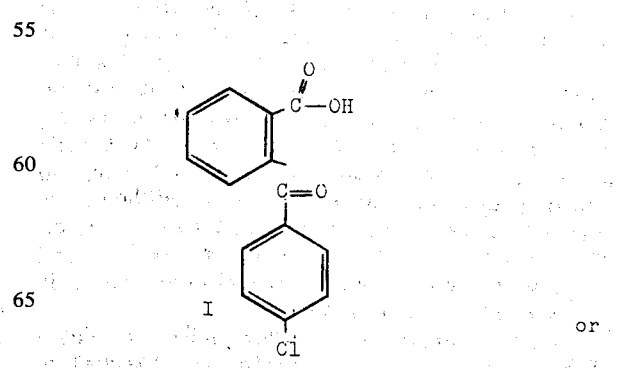

-continued

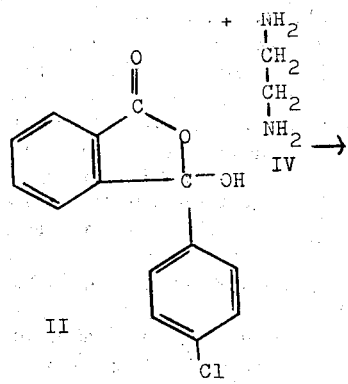

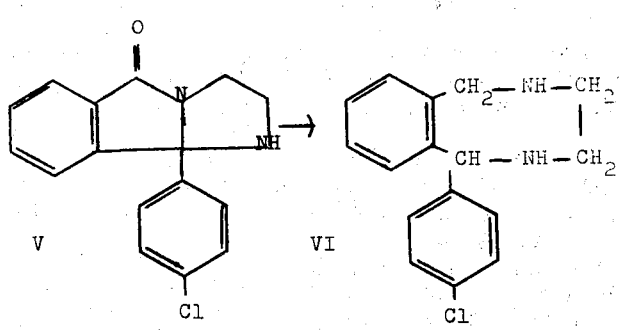

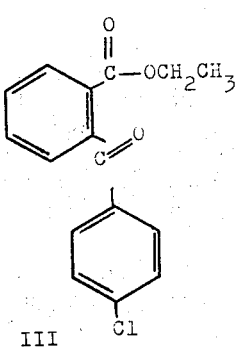

The o-benzoylbenzoic acids [I] either as acids or in their lactol form, i.e., internal ester [II]. or their normal esters [III] and the ethylenediamines [IV], which are the starting materials for the preparation of the compounds of the invention or for carrying out the process of the invention, are known in the art or may be prepared by methods known to those skilled in the art of chemistry. Condensation of the o-benzoylbenzoic acid, lactol, or ester with the ethylenediamine is carried out by refluxing the reactants for from about two or about 16 hours. The condensation is preferably carried out in an inert solvent, such as for example toluene or xylene, or pyridine, but a solvent, while desirable, is not essential if the ethylenediamine is a liquid. The end point of the condensation is reached when no more water distills over, if the o-benzoylbenzoic reactant is in the form of the acid or lactol, and when no more alcohol distills over when the o-benzoylbenzoic reactant is an ester. Preferably, the reaction is performed at a temperature of from about 75°–200° C. The product [V] is separated from solvent and unreacted starting materials and recrystallized from a solvent, such as ethanol or ethyl acetate. The recrystallized condensation product is added in small portions to an ether suspension of a metallic hydride reducing agent, such as for example lithium aluminum hydride, with stirring. Stirring and refluxing are continued for about 15 to 20 hours. Excess hydride reducing agent is decomposed with water. The precipitate is separated, the solution is dried, and the solvent removed under reduced pressure to yield the desired 2,5-benzodiazocine.

It will be apparent to those skilled in the art that both of the aromatic rings of the starting o-benzoylbenzoic acid or ester can be variously substituted with groups that do not interfere with the process of the reaction, such as for example, but not limited thereto, chlorine, alkoxy, hydroxy, nitro, trifluoro, alkyl, amino, and when the o-benzoylbenzoic acid starting material is thus variously substituted, the resulting product will be correspondingly substituted. Therefore, for the process of the invention, these variations on any of the carbons other than the carbons linked to carbonyl are full equivalents of the process as particularly described and claimed.

Similarly, either or both of the carbon atoms of the ethyldiamine starting material can bear alkyl groups, which do not interfere with the course of the reaction, such as methyl, ethyl, propyl, isopropyl, butyl and one, but not both of the amino groups can also bear a similar single alkyl group; one hydrogen atom on one of the nitrogens and two hydrogens on the other nitrogen must be available for the condensation. For the process of the invention, these variations on the starting ethylenediamines are the full equivalents of the invention as particularly described and claimed, and the product of the process will be correspondingly substituted.

It will also be apparent to those skilled in the art that if reactive hydrogen atoms are present on the nitrogen of the fully formed benzodiazocine, that these positions can be acetylated or otherwise acylated with a carboxylic acid anhydride or acid chloride. It will also be apparent that since the fully formed benzodiazocines bear amino nitrogen that these nitrogens will form amine salts and in the applied use aspect, where the amine salt is formed with a pharmaceutically acceptable acid, these salts are the full equivalents of the free base.

Furthermore, it will also be apparent to those skilled in the art that the phenyl group of the o-benzoylbenzoic acid or ester starting material which ultimately forms the "benzo" portion of the benzodiazocine and which is part of the "indol"group of the intermediate isoindol-5-one, can be fully saturated if in lieu of the o-benzoylbenzoic acid starting material a 2-benzoylcyclohexanecarboxylic acid is employed in the process of the invention. Moreover, other groups can be employed in lieu of the phenyl group in the "o-benzoyl" portion of the starting o-benzoylbenzoic acid derivative, such as for example but without limitation thereto, benzyl when the starting compound is o-phenylacetylbenzoic acid, methyl when the starting compound is o-acetylbenzoic acid, ethyl when the starting compound is o-propionylbenzoic acid, etc.; or it can be a heterocyclic group, such as for example, thienyl, when the starting material is an o-thienylbenzoic acid, furyl, when the starting material is an o-furoylbenzoic acid. In the process of the invention such variations are full equivalents of the process as particularly described.

In the applied use characteristic of the principal composition of the invention, such variations on the 2,5-benzodiazocine fully saturated in the non-benzenoid portion and whose nitrogens are tervalent, while affecting the degree of pharmacological activity, do not affect the kind of activity and therefore with respect to the kind of activity are full equivalents of the compositions as particularly described.

When employed in the applied use characteristic of exerting an appetite suppressant effect, the products of the invention are administered in pharmaceutical forms known to those skilled in the art of pharmacy. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablets, the compound is mixed with a carrier having the necessary binding properties in suitable proportions and compacted in the shape and size desired. The powders and tablets preferably contain from 5 or 10 to 99% of the active ingredient. Suitable solid carriers are magnesium carbonate, magnesium stearate, talc, sugar, lactose, pectin, dextrin, starch, gelatin, tracanth, methylcellulose, sodium carboxymethylcellulose, low melting wax, and cocoa butter. Tablets, powders, cachets, and capsules can be used for oral administration and can be incorporated into formulations to obtain delayed or sustained release effects.

Liquid form preparations include solutions, suspensions and emulsions. While the hydrochlorides are soluble, the bases are insoluble in water, but can be dissolved in aqueous organic solvent mixtures that are non-toxic in the amounts used. As an example may be mentioned water propylene glycol solutions for parenteral injection. Liquid preparations can also be formulated in solution, the hydrochlorides usually in water, the bases in aqueous polyethylene glycol. Aqueous suspensions suitable for oral use can be made by dispersing the finely divided bases in water with viscous materials, such as natural or synthetic gums, resins, etc., for example, gum arabic, ion-exchange resins, methylcellulose, sodium carboxymethylcellulose and other well-known suspending agents.

The quantity of compound in a unit dosage form may be adjusted from less than 1 mg. to 1000 mg. (generally within the range of 5 to 250 mg.) and the effective dosage depends upon the stage of the condition being treated, the individual case, and the compound, and will be determined by an attending physician. Generally, a dosage range of from 0.5 to about 150 mg. per kg. of body weight per day constitutes the overall range.

The following examples illustrate the best mode contemplated by the inventor of carrying out the process of the invention and the manner of making and using as intermediates the compositions of the invention.

EXAMPLE 1

Reflux 45 g. of o-benzoylbenzoic acid and 120 ml. of ethylenediamine for 3 hours. Pour the mixture into ice water, allow to stand until the mixture is at room temperature and separate the product by filtration. Recrystallize from ethanol to obtain 9-phenyl-1,2,3,9b-tetrahydro-5H-imidazo-[2,1-a]isoindol-5-one, m.p. 155°–7° C. Elemental analysis confirms the empirical formula $C_{16}H_{14}N_2O$.

Add 40 g. of the condensation product of o-benzoylbenzoic acid and ethylenediamine in small portions to a suspension of 15 g. of lithium aluminum hydride in 1500 ml. of anhydrous either with stirring. Reflux with stirring for 16 hours. Cool and add water carefully to decompose excess hydride. Separate the ether layer, dry over magnesium sulfate, and remove the solvent under reduced pressure to obtain 1,2,3,4,5,6-hexahydro-1-phenyl-2,5-benzodiazocine, m.p. 125° C. To prepare the dihydrochloride, dissolve the base in anhydrous ether and saturate with dry hydrogen chloride. Separate the precipitated solid, and recrystallize from ethanol to obtain 1,2,3,4,5,6-hexahydro-1-phenyl-2,5-benzodiazocine dihydrochloride, m.p. 297° C. (dec.).

EXAMPLE 2

Condense o-benzoylbenzoic acid (10 g.) and N-ethylethylene-diamine (15 ml.) by the procedure of Example 1 to obtain 1-ethyl-9b-phenyl-1,2,3,9b-tetrahydro-5H-imidazo[2,1-a]isoindol-5-one, m.p. 122°–4° C. (elemental analysis confirms the empirical formula $C_{18}H_{18}N_2O$).

EXAMPLE 3

Condense o-(p-chlorobenzoyl)benzoic acid (10 g.) and ethylenediamine (15 ml.) by the procedure of Example 1 to obtain 9b-(p-chlorophenyl)-1,2,3,9b-tetrahydro-5H-imidazo[2,1-a]isoindol-5-one, m.p. 164°–5° C. (elemental analysis confirms the empirical formula $C_{16}H_{13}ClN_2O$), reduce with lithium aluminum hydride, and treat with hydrogen chloride as described in Example 1 to obtain 1-(p-chlorophenyl)-1,2,3,4,5,6-hexahydro-2,5-benzodiazocine dihydrochloride, m.p. 310° C. (dec.) (elemental analysis confirms the empirical formula $C_{16}H_{17}ClN_2.2HCl$).

Resolve 1-(p-chlorophenyl)-1,2,3,4,5,6-hexahydro-2,5-benzodiazocine by fractional crystallization of the d-10-camphor sulfonic acid salt (the 1-salt is more insoluble in ethanol) to obtain the $d$ and $l$ enantiomorphs. Neutralize the camphor sulfonic acid salt with sodium hydroxide and treat with hydrogen chloride to obtain l-1-(p-chlorophenyl)-1,2,3,4,5,6-hexahydro-2,5-benzodiazocine, dihydrochloride, m.p. 303° C. (dec.), $\alpha_D^{25}$ -118.3° ($H_2O$) and d-1-(p-chlorophenyl)-1,2,3,4,5,6-hexahydro-2,5-benzodiazocine, dihydrochloride, m.p. 303° C. (dec.) $\alpha_D^{25}$ +115.9° ($H_2O$).

EXAMPLE 4

Condense o-(p-chlorobenzoyl)benzoic acid (13 g.) and N-ethylethylenediamine (15 ml.) by the procedure of Example 1 to obtain 1-ethyl-9b-(p-chlorophenyl)-1,2,3,9b-tetrahydro-5H-imidazo[2,1-a]isoindol-5-one, m.p. 114° C. (elemental analysis confirms the empirical formula $C_{18}H_{17}ClN_2O$).

EXAMPLE 5

Condense methyl-o-(p-methoxybenzoyl)benzoate (7 g.) and ethylenediamine (8 ml.) by procedure of Example 1 to obtain 9b-p-methoxyphenyl)-1,2,3,9b-tetrahydro-5H-imidazo[2,1-*a*]*isoindol*-5-one, m.p. 159° C. (elemental analysis confirms the empirical formula $C_{17}H_{16}N_2O_2$), reduce with lithium aluminum hydride, and treat with hydrogen chloride as described in Example 1 to obtain 1,2,3,4,5,6-hexahydro-1-(p-methoxyphenyl)-2,5-benzodiazocine dihydrochloride, m.p. 260° C.

EXAMPLE 6

Condense o-benzoylbenzoic acid (22 g.) and 2,3-diaminobutane in toluene (400 ml.) by the procedure of Example 1 to obtain 2,3-dimethyl-9b-phenyl-1,2,3,9b-tetrahydro-5H-imidazo[2,1-a]isoindol-5-one, m.p. 162°–4° C. (elemental analysis confirms the empirical formula $C_{18}H_{18}N_2O$) and reduce with lithium aluminum hydride as described in Example 1 to obtain 3,4-dimethyl-1,2,3,4,5,6-hexahydro-1-phenyl-2,5-benzodiazocine.

EXAMPLE 7

Condense 2-benzoylcyclohexanecarboxylic (15 g.) and ethylenediamine (30 ml.) by the procedure of Example 1 to obtain 9b-phenyl-1,2,3,5a,6,7,8,9,9a,9b-decahydro-5H-imidazo[2,1-a]isoindol-5-one, m.p. 170° C. (elemental analysis confirms the empirical formula $C_{16}H_{20}N_2O$ and reduce with lithium aluminum hydride as described in Example 1 to obtain 1,2,3,4,5,6,6a, 7,8,9,10,10a-dodecahydro-1-phenyl-2,5-benzodiazocine.

EXAMPLE 8

Condense 3-benzyl-3-hydroxyphthalide (15 g.) and ethylenediamine (30 ml.) by the procedure of Example 1 to obtain 9b-benzyl-1,2,3,9b-tetrahydro-5H-imidazo[2,1-a]isoindol-5-one, m.p. 115°–117° C. (elemental analysis confirms the empirical formula $C_{17}H_{16}N_2O$), reduce with lithium aluminum hydride and treat with hydrogen chloride as described in Example 1 to obtain 1-benzyl-1,2,3,4,5,6-hexahydro-2,5-benzodiazocine dihydrochloride, m.p. 238°–40° C.

EXAMPLE 9

Condense 2-benzoyl-4-nitrobenzoic acid with ethylenediamine by the procedure of Example 1 to obtain 8-nitro-9b-phenyl-1,2,3,9b-tetrahydro-5H-imidazo[2,1-a]isoindol-5-one, m.p. 203° C.

EXAMPLE 10

Condense o-(p-fluorobenzoyl)benzoic acid with ethylenediamine by the procedure of Example 1 to obtain 9b-(p-fluorophenyl)-1,2,3,9b-tetrahydro-5H-imidazo[2,1-a]isoindol-5-one, reduce with lithium aluminum hydride and treat with hydrogen chloride as described in Example 1 to obtain 1-(p-fluorophenyl)-1,2,3,4,5,6-hexahydro-2,5-benzodiazocine, dihydrochloride, m.p. 303° C. (dec.).

EXAMPLE 11

Condense o-(2-thienoyl)benzoic acid with ethylenediamine by the procedure of Example 1 to obtain 9b-(2-thienyl)-1,2,3,9b-tetrahydro-5H-imidazo[2,1-a]isoindol-5-one and reduce with lithium aluminum hydride as described in Example 1 to obtain 1,2,3,4,5,6-hexahydro-1-(2-thienyl)-2,5-benzodiazocine, m.p. 148° C. The dihydrochloride melts at 241° C.

EXAMPLE 12

In the following table, condense Keto-acid A with Amine B by the procedure of Example 1 to obtain Intermediate C, and reduce Intermediate C as described in Example 1 to obtain Product D:

| Keto-Acid | Amine B | Intermediate C | Product D |
| --- | --- | --- | --- |
| o-(3-thienoyl)benzoic acid | ethylenediamine | 9b-(3-thienyl)-1,2,3,9b-tetrahydro-5H-imidazo[2,1-a]isoindol-5-one | 1,2,3,4,5,6-hexahydro-1-(3-thienyl)-2,5-benzodiazocine |
| o-(3-furoyl)benzoic acid | ethylenediamine | 9b-(3-furyl)-1,2,3,9b-tetrahydro-5H-imidazo[2,1-a]isoindol-5-one | 1,2,3,4,5,6-hexahydro-1-(3-furyl)-2,5-benzodiazocine |
| ethyl o-(m-trifluoromethylbenzoyl)benzoate | ethylenediamine | 9b-(m-trifluoromethylphenyl-1,2,3,9b-tetrahydro-5H-imidazo[2,1-a]isoindol-5-one | 1,2,3,4,5,6-hexahydro-1-(m-trifluoromethylphenyl)-2,5-benzodiazocine |
| 2-benzoyl-5-methyl-benzoic acid | ethylenediamine butane | 7-methyl-9b-phenyl-1,2,3,9b-tetrahydro-5H-imidazo[ | 1,2,3,4,5,6-hexahydro-8-methyl- |
| acid | isoindol-5-one | 1-phenyl-2,5-benzodiazocine | |
| 2-benzoyl-5-methoxy-benzoic acid | ethylenediamine | 7-methoxy-9b-phenyl-1,2,3,9b-tetrahydro-5H-imidazo[2,1-a]isoindol-5-one | 1,2,3,4,5,6-hexahydro-8-methoxy-1-phenyl-2,5-benzodiazocine |
| 2-benzoyl-5-trifluoromethylbenzoic acid | ethylenediamine | 9b-phenyl-1,2,3,9b-tetrahydro-7-trifluoromethylphenyl-5H-imidazo[2,1-a]isoindol-5-one | 1,2,3,4,5,6-hexahydro-1-phenyl-8-trifluoromethylphenyl-2,5-benzodiazocine |
| 4-amino-2-benzoylbenzoic acid | ethylenediamine | 8-amino-9b-phenyl-1,2,3,9b-tetrahydro-5H-imidazo[2,1-a]isoindol-5-one | 9-amino-1,2,3,4,5,6-hexahydro-1-phenyl-2,5-benzodiazocine |
| 2-(p-chlorobenzoyl)-4,5-dimethoxybenzoic acid | ethylenediamine | 9b-(p-chlorophenyl)-7,8-dimethoxy-1,2,3,9b-tetrahydro-5H-imidazo[2,1-a]isoindol-5-one | 1-(p-chlorophenyl)-8,9-dimethoxy-1,2,3,4,5,6-hexahydro-2,5-benzodiazocine |
| 2-propionylbenzoic acid | 2,3-diaminobutane | 2,3-dimethyl-9b-ethyl-1,2,3,9b-tetrahydro-5H-imidazo[2,1-a]isoindol-5-one | 3,4-dimethyl-1-ethyl-1,2,3,4,5,6-hexahydro-2,5-benzodiazocine |
| 5-amino-2-acetylbenzoic acid | N-methyl-ethylene-diamine | 7-amino-1,9b-dimethyl-1,2,3,9b-tetrahydro-5H-imidazo[2,1-a]isoindol-5-one | |
| 2-(p-trifluoromethylbenzoyl)benzoic acid | N-ethyl-ethylene-diamine | 1-ethyl-9b-(p-trifluoromethylphenyl)-1,2,3,9b-tetrahydro-5H-imidazo[2,1-a]isoindol-5-one | |
| 4-chloro-2-(p-methoxybenzoyl)benzoic acid | N-methyl-ethylene-diamine | 8-chloro-9b-(p-methoxyphenyl-1-methyl-1,2,3,9b-tetrahydro-5H-imidazo[2,1-a]isoindol-5-one | |

-continued

| Keto-Acid | Amine B | Intermediate C | Product D |
| --- | --- | --- | --- |
| 2-(p-methylbenzoyl)-5-methyl-benzoic acid | ethylenediamine | 7-methyl-9b-(p-methylphenyl)-1,2,3,9b-tetrahydro-5H-imidazo-[2,1-a]isoindol-5-one | 8-methyl-1-(p-methylphenyl)-2,5-benzodiazocine |
| 2-benzoyl-4,5-dichloro-benzoic acid | ethylenediamine | 7,8-dichloro-9b-phenyl-1,2,3,9b-tetrahydro-5H-imidazo[2,1-a]isoindol-5-one | 8,9-dichloro-1,2,3,4,5,6-hexahydro-1-phenyl-2,5-benzodiazocine |
| o-(2-thienoyl)benzoic acid | 2,3-diaminobutane | 2,3-dimethyl-9b-(2-thienyl)-1,2,3,9b-tetrahydro-5H-imidazo[2,1-a]isoindol-5-one, m.p. 152° C | 3,4-dimethyl-1,2,3,4,5,6-hexahydro-1-(2-thienyl)-2,5-benzodiazocine |
| o-(p-hydroxybenzoyl)benzoic acid | ethylenediamine | 9b-(p-hydroxyphenyl)-1,2,3,9b-tetrahydro-5H-imidazo[2,1-a]isoindol-5-one, m.p. 266–8° C | 1-(p-hydroxyphenyl)-1,2,3,4,5,6-hexahydro-2,5-benzodiazocine |
| o-(3-amino-4-chlorobenzoyl)benzoic acid | ethylenediamine | 9b-(3-amino-4-chlorophenyl)-1,2,3,9b-tetrahydro-5H-imidazo[2,1-a]isoindol-5-one, m.p. 172–4° C | 1-(3-amino-4-chlorophenyl)-1,2,3,4,5,6-hexahydro-2,5-benzodiazocine |
| o-(3-amino-4-chlorobenzoyl)benzoic acid | N-methyl-ethylenediamine | 9b-(3-amino-4-chlorophenyl)-1-methyl-1,2,3,9b-tetrahydro-5H-imidazo[2,1-a]isoindol-5-one, m.p. 176–8° C | |
| o-(p-chlorobenzoyl)benzoic acid | N-methyl-ethylenediamine | 9b-(p-chlorophenyl)-1-methyl-1,2,3,9b-tetrahydro-5H-imidazo[2,1-a]isoindol-5-one, m.p. 134– 6° C. | |
| o-(2,4-dimethoxybenzoyl)benzoic acid | ethylenediamine | 9b-(2,4-dimethoxyphenyl)-1,2,3,9b-tetrahydro-5H-imidazo[2,1-a]isoindol-5-one, m.p. 173–5° C | 1-(2,4-dimethoxyphenyl)-1,2,3,4,5,6-hexahydro-2,5-benzodiazocine |
| o-(3,4-dichlorobenzoyl)benzoic acid | ethylenediamine | 9b-(3,4-dichlorophenyl)-1,2,3,9b-tetrahydro-5H-imidazo[2,1-a]isoindol-5-one, m.p. 219–221° C | 1-(3,4-dichlorophenyl)-1,2,3,4,5,6-hexahydro-2,5-benzodiazocine dihydrochloride, m.p. 320° C |
| o-(2,4-dichlorobenzoyl)benzoic acid | ethylenediamine | 9b-(2,4-dichlorophenyl)-1,2,3,9b-tetrahydro-5H-imidazo[2,1-a]isoindol-5-one, m.p. 173–5° C | 1-(2,4-dichlorophenyl)-1,2,3,4,5,6-hexahydro-2,5-benzodiazocine dihydrochloride, m.p. 306° C |
| o-(m-chlorobenzoyl)benzoic acid | ethylenediamine | 9b-(m-chlorophenyl)-1,2,3,9b-tetrahydro-5H-imidazo[2,1-a]isoindol-5-one, m.p. 173–5° C | 1-(m-chlorophenyl)-1,2,3,4,5,6-hexahydro-2,5-benzodiazocine dihydrochloride, m.p. 303° C |
| o-(p-bromobenzoyl)benzoic acid | ethylenediamine | 9b-(p-bromophenyl)-1,2,3,9b-tetrahydro-5H-imidazo[2,1-a]isoindol-5-one, m.p. 158–160° C | 1-(p-bromophenyl-1,2,3,4,5,6-hexahydro-2,5-benzodiazocine dihydrochloride, m.p. 319° C |
| o-(5,6,7,8-tetrahydro-2-naphthoyl)benzoic acid | ethylenediamine | 9b-(5,6,7,8-tetrahydro-2-naphthyl)-1,2,3,9b-tetrahydro-5H-imidazo[2,1-a]isoindol-5-one, m.p. 165–7° C | 1-(5,6,7,8-tetrahydro-2-naphthyl)-1,2,3,4,5,6-hexahydro-2,5-benzodiazocine, m.p. 109–110.5° C |

| Keto-Acid A | Amine | Intermediate C | Product D |
| --- | --- | --- | --- |
| o-(p-chlorobenzoyl)-benzoic acid | 1,2-diaminopropane | 1) 9b-(p-chlorophenyl)-3-methyl-1,2,3,9b-tetrahydro-5H-imidazo[2,1-a]isoindol-5-one, m.p. 130° C | 1) 1-(p-chlorophenyl)-1,2,3,4,5,6-hexahydro-4-methyl-2,5-benzodiazocine dihydrochloride, m.p. 306–7° C (dec.) |
|  |  | 2) 9b-(p-chlorophenyl)-2-methyl-1,2,3,9b-tetrahydro-5H-imidazo-[2,1-a]isoindol-5-one, m.p. 192° C | 2) 1-(p-chlorophenyl)-1,2,3,4,5,6-hexahydro-3-methyl-2,5-benzodiazocine dihydrochloride |
| o-benzoylbenzoic acid | 1,2-Diaminopropane | 3-methyl-9b-phenyl-1,2,3,9b-tetrahydro-5H-imidazo[2,1-a]isoindol-5-one, m.p. 149–151° C | 1,2,3,4,5,6-hexahydro-4-methyl-1-phenyl-2,5-benzodiazocine dihydrochloride, m.p. 312° C (dec.). |
| o-(p-trifluoromethylbenzoyl)benzoic acid | ethylenediamine | 1,2,3,9b-tetrahydro-9b-(p-trifluoromethylphenyl)-5H-imidazo[2,1-a]isoindol-5-one, m.p. 193–4° C | 1,2,3,4,5,6-hexahydro-1-(p-trifluoromethylphenyl)-2,5-benzodiazocine dihydrochloride, m.p. 322° C (dec.) |
| o-(3-bromo-4-methylbenzoyl)benzoic acid | ethylenediamine | 9b-(3-bromo-4-methylphenyl)-1,2,3,9b-tetrahydro-5H-imidazo[2,1-a]isoindol-5-one, m.p. 191–3° C | 1-(3-bromo-4-methylphenyl)-1,2,3,4,5,6-hexahydro-2,5-benzodiazocine dihydrochloride, m.p. 310° C (dec.) |
| o-(m-trifluoromethylbenzoyl)benzoic acid | ethylenediamine | 1,2,3,9b-tetrahydro-9b-(m-trifluoromethylphenyl)-5H-imidazo[2,1-a]isoindol-5-one, m.p. 140–2° C | 1,2,3,4,5,6-hexahydro-1-(m-trifluoromethylphenyl)-2,5-benzodiazocine dihydrochloride |
| o-(p-chlorobenzoyl)benzoic acid | 1,2-diamino-2-methylpropane | 9b-(p-chlorophenyl)-3,3-dimethyl-1,2,3,9b-tetrahydro-5H-imidazo[2,1-a]isoindol-5-one, m.p. 132–3° C | 1-(p-chlorophenyl)-1,2,3,4,5-hexahydro-4,4-dimethyl-2,5-benzodiazocine dihydrochloride |
| o-(p-chlorobenzoyl)benzoic acid | 2,3-diphenyl-ethylenediamine | 9b-(p-chlorophenyl)-2,3-diphenyl-1,2,3,9b-tetrahydro-5H-imidazo[2,1-a]isoindol-5-one, m.p. 227–9° C | 1-(p-chlorophenyl)-1,2,3,4,5,6-hexahydro-3,4-diphenyl-2,5-benzodiazocine dihydrochloride |
| o-(p-ethylbenzoyl)benzoic acid | ethylenediamine | 9b-(p-ethylphenyl)-1,2,3,9b-tetrahydro-5H-imidazo[2,1-a]isoindol-5-one, m.p. 128–130° C | 1-(p-ethylphenyl)-1,2,3,4,5,6-hexahydro-2,5-benzodiazocine dihydrochloride |

The subject matter which the applicant regards as his invention is particularly pointed out and distinctly claimed as follows:

1. 9b-phenyl-1,2,3,9b-tetrahydro-5H-imidazo[2,1-a]isoindol-5-one.

2. 9b-(p-chlorophenyl)-1,2,3,9b-tetrahydro-5H-imidazo[2,1-a]isoindol-5-one.

3. A process for preparing a 9b-phenyl-1,2,3,9b-tetrahydro-5H-imidazo[2,1-a]isoindol-5-one which comprises contacting an o-benzoylbenzoic acid, in an inert solvent, with a diamine of the formula $H_2N(CHR)_2NH_2$, wherein each R is, independently, hydrogen or lower alkyl, and refluxing the same in said inert solvent.

4. A process of claim 3 wherein the diamine is ethylene diamine.

* * * * *